US006913732B2

United States Patent
Sha et al.

(10) Patent No.: US 6,913,732 B2
(45) Date of Patent: Jul. 5, 2005

(54) MICROPLATE FOR PERFORMING CRYSTALLOGRAPHY STUDIES AND METHODS FOR MAKING AND USING SUCH MICROPLATES

(75) Inventors: Ma Sha, Cambridge, MA (US); Kathy Youngbear, Cambridge, MA (US)

(73) Assignee: Corning Incorporated, Corning, NY (US)

( * ) Notice: Subject to any disclaimer, the term of this patent is extended or adjusted under 35 U.S.C. 154(b) by 267 days.

(21) Appl. No.: 09/811,999

(22) Filed: Mar. 19, 2001

(65) Prior Publication Data

US 2002/0141905 A1 Oct. 3, 2002

(51) Int. Cl.$^7$ ................................................ B01L 3/00
(52) U.S. Cl. ........................ 422/102; 422/99; 422/104; 422/245.1; 117/206
(58) Field of Search ........................... 435/288.2, 288.3, 435/288.4; 117/206; 422/245.1, 99–104

(56) References Cited

U.S. PATENT DOCUMENTS

| | | | | |
|---|---|---|---|---|
| 5,096,676 | A | * | 3/1992 | McPherson et al. ......... 117/206 |
| 5,419,278 | A | | 5/1995 | Carter ........................ 117/206 |
| 5,604,130 | A | * | 2/1997 | Warner et al. ............ 435/286.7 |
| 5,858,309 | A | | 1/1999 | Mathus et al. ............... 422/102 |
| 5,910,287 | A | | 6/1999 | Cassin et al. ............... 422/102 |
| 6,027,695 | A | | 2/2000 | Oldenburg et al. .......... 422/102 |
| 6,063,282 | A | * | 5/2000 | Moulton ..................... 210/650 |
| 6,063,338 | A | | 5/2000 | Pham et al. .................. 422/61 |
| 6,171,780 | B1 | | 1/2001 | Pham et al. .................... 435/4 |
| 6,229,603 | B1 | | 5/2001 | Coassin et al. .............. 356/246 |
| 6,296,673 | B1 | | 10/2001 | Santarsiero et al. ........... 23/295 |
| 6,340,589 | B1 | * | 1/2002 | Turner et al. ............. 435/287.2 |
| 6,379,625 | B1 | * | 4/2002 | Zuk, Jr. ....................... 422/101 |
| 6,426,050 | B1 | | 7/2002 | Pham et al. ................. 422/104 |
| 6,433,868 | B1 | | 8/2002 | Brunner et al. ............. 356/300 |
| 6,503,456 | B1 | * | 1/2003 | Knebel ........................ 422/102 |
| 2002/0025573 | A1 | | 2/2002 | Maher et al. ............. 435/287.1 |
| 2002/0062783 | A1 | | 5/2002 | Bray ........................... 117/68 |
| 2004/0141895 | A1 | * | 7/2004 | Sha ........................... 422/245.1 |

FOREIGN PATENT DOCUMENTS

| | | |
|---|---|---|
| EP | 0408280 A2 * | 1/1991 |
| WO | WO 99/19067 A1 | 4/1999 |
| WO | WO 00/00678 A1 | 1/2000 |
| WO | WO 00/78445 A1 | 12/2000 |
| WO | WO 01/88231 A1 | 11/2001 |
| WO | WO 02/066713 A1 | 8/2002 |

OTHER PUBLICATIONS

Hampton Research–Plates–CrystalClear Strips (http:www.hamptonresearch.com/catalog/3128.html) 2 pages downloaded Jan. 18, 2001.

(Continued)

*Primary Examiner*—Jill Warden
*Assistant Examiner*—Dwayne K Handy
(74) *Attorney, Agent, or Firm*—Joanne N. Pappas; William J. Tucker

(57) ABSTRACT

The present invention includes a microplate for performing crystallography studies and methods for making and using such microplates. In particular, the microplate has a frame which includes a plurality of wells formed therein. Each well includes a first well and a second well. The first well includes a relatively small reservoir having a substantially concaved form capable of receiving a protein solution and a reagent solution. The second well includes a relatively large reservoir capable of receiving a reagent solution that has a higher concentration than the reagent solution within the first well, wherein the protein solution and the reagent solution within the first well interact with the reagent solution within the second well via a vapor diffusion process which enables the formation of protein crystals within the first well. The microplate may be sized so that it can be handled by a robotic handling system and/or a liquid handling system.

9 Claims, 6 Drawing Sheets

OTHER PUBLICATIONS

Hampton Research–Plates–Cryschem Plate (http:www.hamptonresearch.com/catalog/3158.html) 2 pages downloaded Jan. 18, 2001.

Raymond C. Stevens "High–throughput protein crystallization" Current Opinion in Structural Biology, vol. 10, issue 5, pp. 558–563, Oct. 1, 2000.

"Q Plate II, Q Plate and Q Plate Polypropylene" www.hamptonresearch.com, 5 pages, copyrighted 2001.

"CrystalClear Strips" www.hamptonresearch.com, 2 pages, copyrighted 2001.

"CombiClover Crystallization Plate" www.yashimachem.co.jp/products/emerald/combic.htm, 2 pages, downloaded Nov. 2002.

"Macromolecular Crystallography" www.jenabioscience.com, 4 pages, downloaded Nov. 2002.

Harlos K. "Micro–Bridges for Sitting–Drop Crystallizations", Journal of Applied Crystallography, vol. 25, abstract, Aug. 1, 1992.

"Micro–Bridges and Micro–Bridges Polypropylene" www.hamptonresearch.com, 2 pages, copyrighted 2001.

* cited by examiner

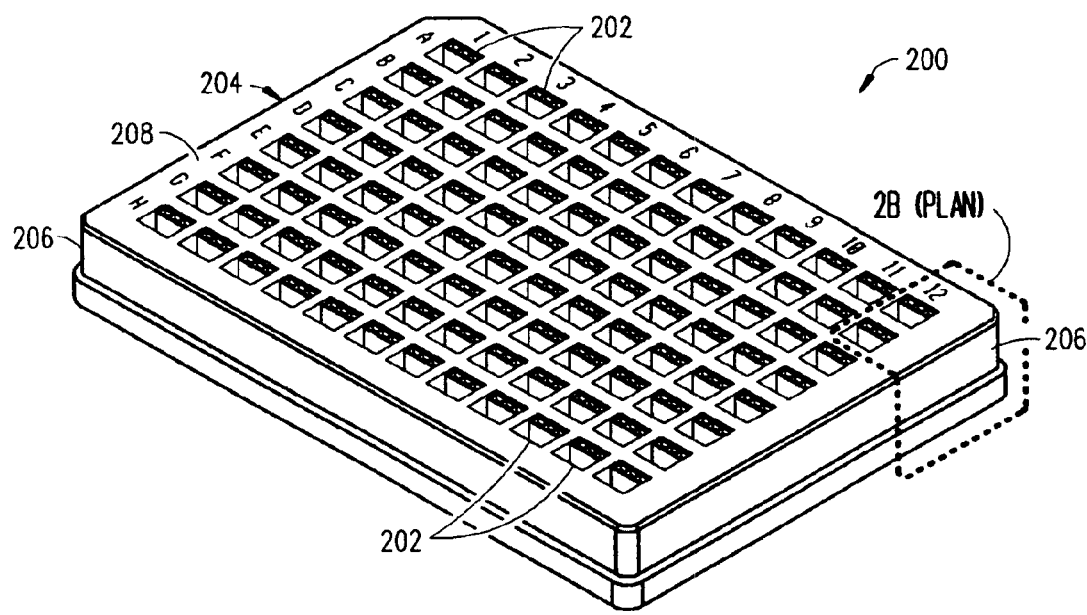
FIG. 2A (PRIOR ART)
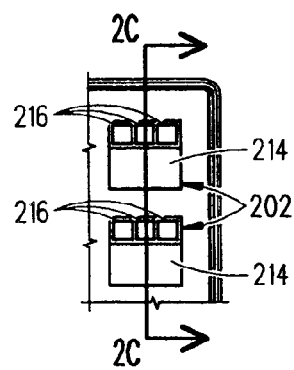
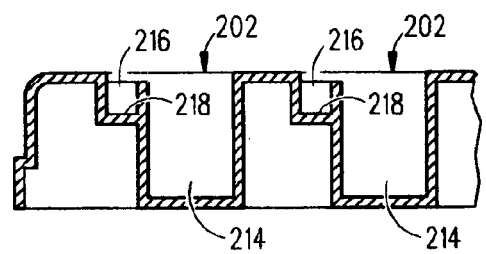
FIG. 2B (PRIOR ART)
FIG. 2C (PRIOR ART)

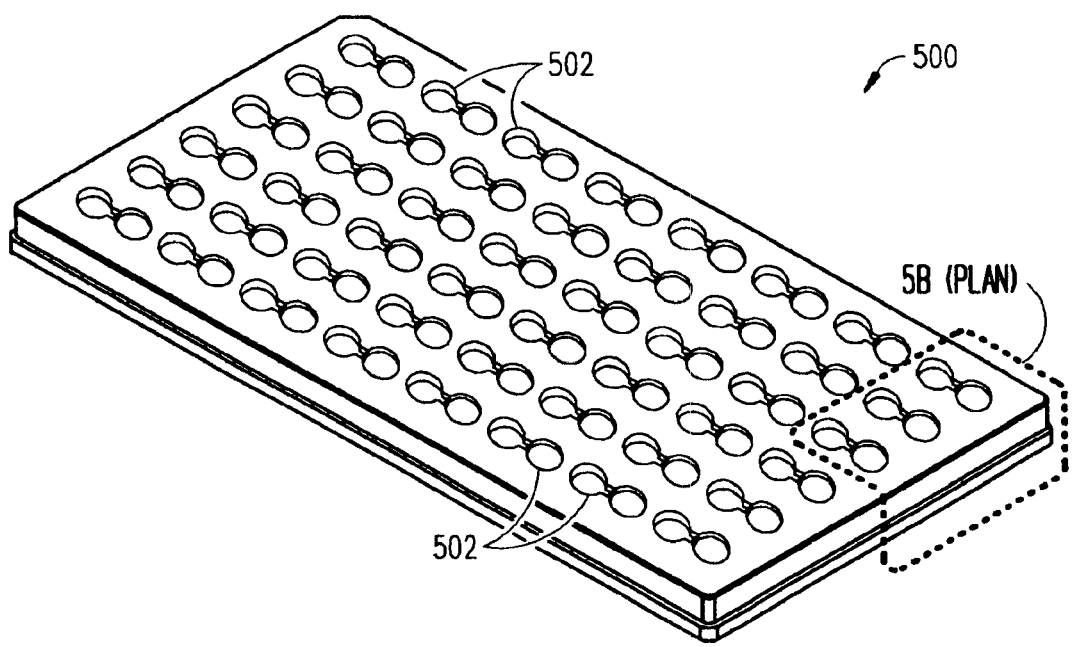
FIG. 5A
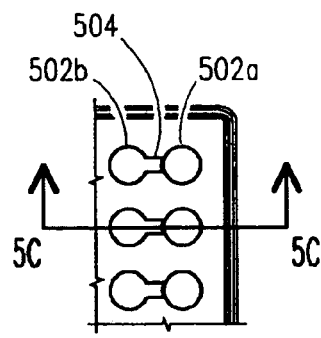 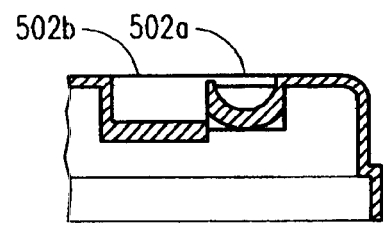
FIG. 5B  FIG. 5C

MICROPLATE FOR PERFORMING CRYSTALLOGRAPHY STUDIES AND METHODS FOR MAKING AND USING SUCH MICROPLATES

BACKGROUND OF THE INVENTION

1. Field of the Invention

The present invention relates in general to the biotechnology field and, in particular, to a microplate for assaying samples and methods for making and using such microplates.

2. Description of Related Art

Today biochemical studies associated with growing protein and other biological crystals are carried out on a large scale in both industry and academia, so it is desirable to have an apparatus that allows these studies to be performed in a convenient and inexpensive fashion. Because they are relatively easy to handle and low in cost, microplates are often used for such studies. Microplates typically consist of a matrix of wells formed of a polymeric material. Examples of two traditional sitting drop protein crystallography microplates are briefly discussed below with respect to FIGS. 1 and 2.

Referring to FIGS. 1A and 1B (PRIOR ART), there are respectively illustrated a perspective view and a cross-sectional side view of a traditional microplate 100 manufactured and sold by Hampton Research. As illustrated, the Hampton Research microplate 100 is a 24 well sitting drop microplate that includes an array of twenty-four wells 102, each of which may receive a sample of a protein solution to be assayed.

As seen from the perspective view of FIG. 1A, the Hampton Research microplate 100 includes a frame 104 that supports the wells 102. The frame 104 which is rectangular in shape includes an outer wall 106 and a top planar surface 108 extending between the outer wall 106 and the wells 102. The wells 102 as shown have circular cross-sections in a plane parallel to the top planar surface 108. The outer wall 106 that defines the outer periphery of the frame 104 has a bottom edge 110 that extends below the wells 102. Thus, when the Hampton Research microplate 100 is placed on a support surface, it is supported by the bottom edge 110 with the wells 102 being raised above the support surface to protect them from damage. As illustrated, the outer wall 106 also has a rim 112 to accommodate the skirt of a microplate cover (not shown).

Referring to FIG. 1B, each well 102 includes outer sidewalls 114, a bottom 116 and a post 118. The post 118 located in the center of the well 102 includes a concaved reservoir 120 in which a protein solution and a reagent solution are placed. A portion of the area in the well 102 around the post 118 receives a reagent solution that has a higher concentration than the reagent solution within the concaved reservoir 120. The configuration of the well 102 then enables the protein solution and the reagent solution within the concaved reservoir 120 to interact with the reagent solution around the post 118 via a vapor diffusion process which enables the formation of protein crystals within the concaved reservoir 120. It should be noted the Hampton Research also manufactures and sales a 96 well strip microplate which is similar to the 24 well microplate 100 except that the wells are shrunk down in size.

Referring to FIGS. 2A through 2C (POSSIBLE PRIOR ART), there are respectively illustrated a perspective view, a partial top view and a cross-sectional side view of a traditional microplate 200 manufactured and sold by C. A. Greiner & Sohne Gesellschaft m.b.H. Basically, the Greiner microplate 200 is a 96 well sitting drop microplate where each well 202 may receive up to three samples of protein solutions to be studied. As seen from the perspective view of FIG. 2A, the Greiner microplate 200 includes a frame 204 that supports the wells 202. The frame 204 which is rectangular in shape includes an outer wall 206 that defines the periphery of the frame 204 and a top planar surface 208 extending between the outer wall 206 and the wells 202. The wells 202 as shown have rectangular cross-sections in a plane parallel to the top planar surface 208.

Referring to FIG. 2B and 2C, each well 202 includes a relatively large reservoir 214 and three relatively small reservoirs 216. Each small reservoir 216 includes a flat bottom 218 on which there is deposited a protein solution and a reagent solution. The large reservoir 214 located next to the small reservoirs 216 receives a reagent solution that has a higher concentration than the reagent solutions within the small reservoirs 216. The configuration of the well 202 then enables the protein solution and the reagent solution within each of the small reservoirs 216 to interact with the reagent solution within the large reservoir 214 via a vapor diffusion process which enables the formation of protein crystals within each of the small reservoirs 216.

Unfortunately, the traditional microplates 100 and 200 have many disadvantages attributable to their configurations and their materials of construction such that they are not well suited for protein crystallography studies. For instance, the traditional microplates 100 and 200 are not configured and sized to be handled by a robotic handling system and liquid handling system. Accordingly, there is a need for a microplate that is designed to enable a researcher to effectively conduct protein crystallography studies. This need and other needs are satisfied by the microplate and the methods of the present invention.

BRIEF DESCRIPTION OF THE INVENTION

The present invention includes a microplate for performing crystallography studies and methods for making and using such microplates. In particular, the microplate has a frame which includes a plurality of wells formed therein. Each well includes a first well and a second well. The first well includes a relatively small reservoir having a substantially concaved form capable of receiving a protein solution and a reagent solution. The second well includes a relatively large reservoir capable of receiving a reagent solution that has a higher concentration than the reagent solution within the first well, wherein the protein solution and the reagent solution within the first well interact with the reagent solution within the second well via a vapor diffusion process which enables the formation of protein crystals within the first well. The microplate may be sized so that it can be handled by a robotic handling system and/or a liquid handling system.

BRIEF DESCRIPTION OF THE DRAWINGS

A more complete understanding of the present invention may be had by reference to the following detailed description when taken in conjunction with the accompanying drawings wherein:

FIGS. 2A through 2C (POSSIBLE PRIOR ART) respectively illustrate a perspective view, a partial top view and a cross-sectional side view of a traditional microplate 200 manufactured and sold by C. A. Greiner & Sohne Gesellschaft m.b.H;

FIGS. 5A through 5C respectively illustrate a perspective view, partial top view and a cross-sectional side view of a third embodiment of a microplate in accordance with the present invention;

DETAILED DESCRIPTION OF THE DRAWINGS

Referring to FIGS. 3–7, there are disclosed three embodiments of a microplate and preferred methods for making and using the microplate. Although the microplate of the present invention is described as having ninety-six functional wells (first and second embodiments) and forty-eight functional wells (third embodiment) arranged in a grid having a plurality of rows and columns, it should be understood that the present invention is not limited to these arrangements. Instead, the present invention can be implemented in any type of microplate arrangement and is not limited to any specific number of wells.

Figure 1A:
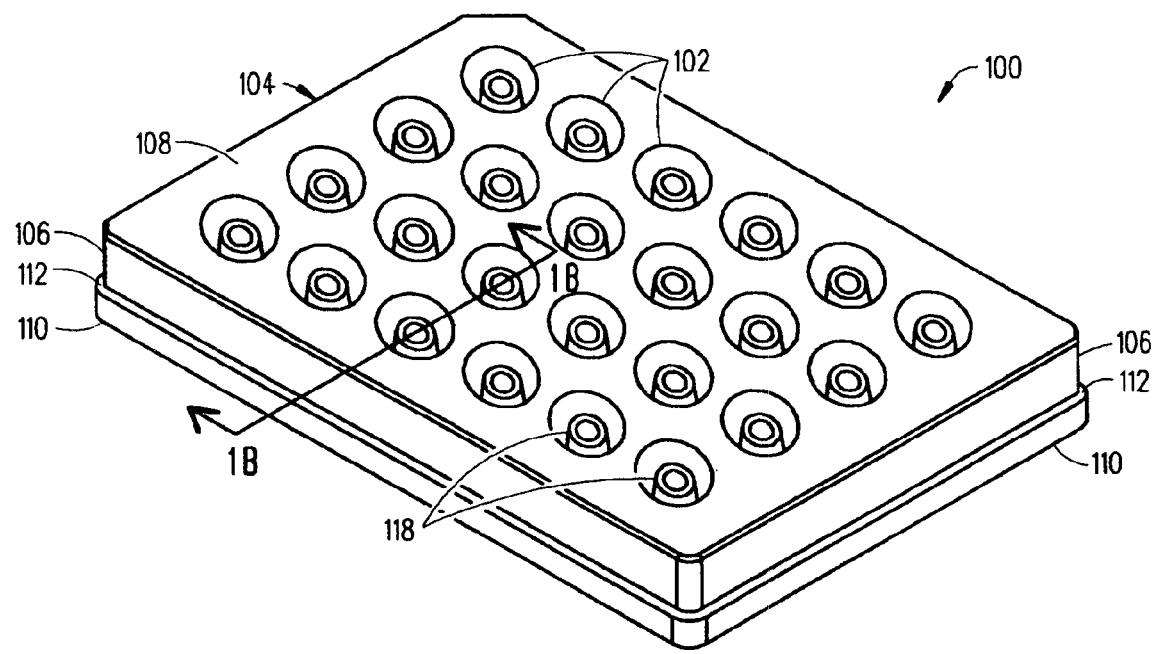
FIGS. 1A and 1B (PRIOR ART) respectively illustrate a perspective view and a cross-sectional side view of a traditional microplate manufactured and sold by Hampton Research.
Figure 1B:
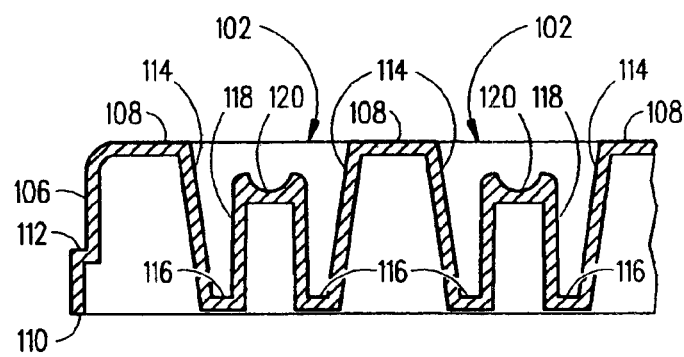
Figure 3A:
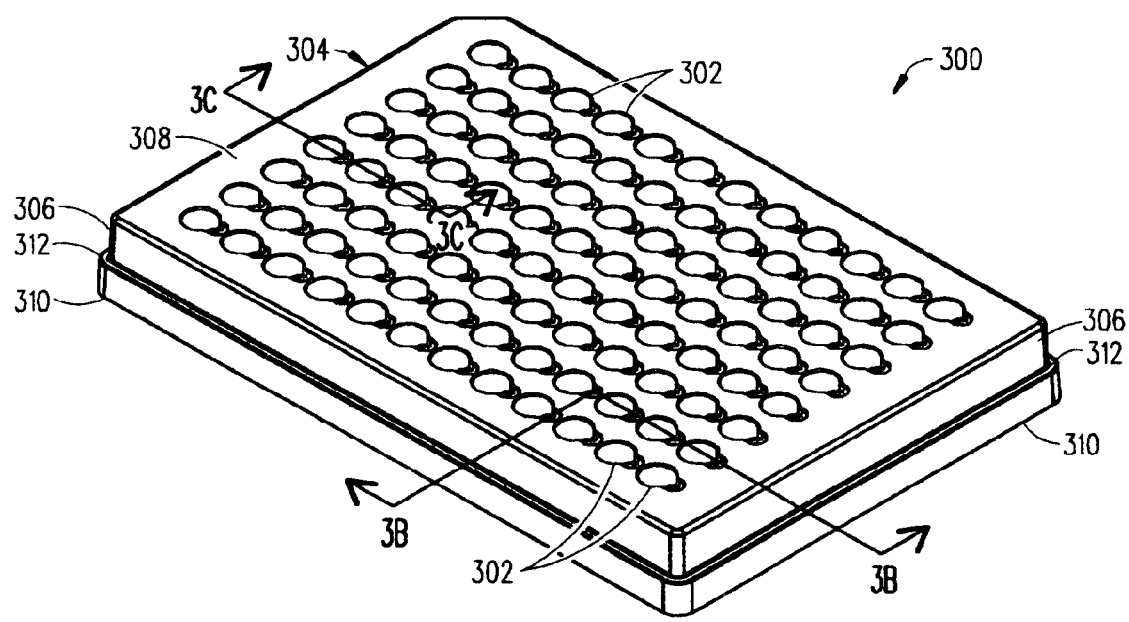
FIGS. 3A through 3C respectively illustrate a perspective view, cut-away partial perspective view and a cross-sectional side view of a first embodiment of a microplate in accordance with the present invention.
Figure 3B:
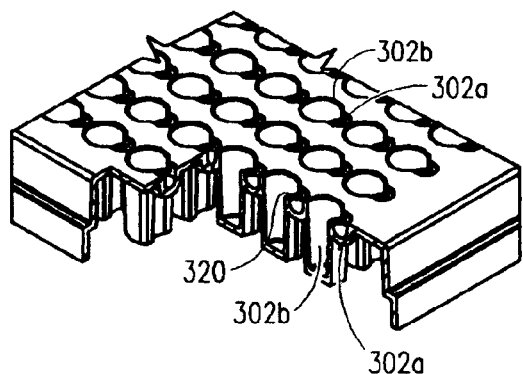
Figure 3C:
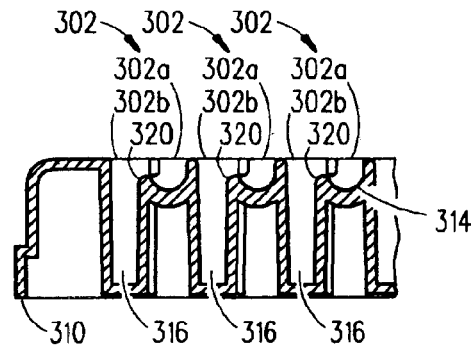

Referring to FIGS. 3A through 3C, there are respectively illustrated a perspective view, a cut-away partial perspective view and a cross-sectional side view of a first embodiment of a microplate 300 in accordance with the present invention. As illustrated, the microplate 300 is a 96 well high-throughput crystallography microplate that includes an array of ninety-six wells 302, each of which may receive a sample of a protein solution to be studied.

The microplate 300 includes a frame 304 that supports the wells 302. The frame 304 which is rectangular in shape includes an outer wall 306 and a top planar surface 308 extending between the outer wall 306 and the wells 302. However, it should be understood that the frame 304 can be provided in any number of other geometrical shapes (e.g., triangular or square) depending on the desired arrangement of the wells 302. As illustrated, the outer wall 306 that defines the outer periphery of the frame 304 has a bottom edge 310 that extends below the wells 302. Thus, when the microplate 300 is placed on a support surface, it is supported by the bottom edge 310 with the wells 302 being raised above the support surface to protect them from damage. The outer wall 306 also has a rim 312 to accommodate the skirt of a microplate cover (not shown).

Referring to FIGS. 3B and 3C, each well 302 has two overlapping circular wells 302a and 302b both Of which are located in a plane parallel to the top planar surface 308. The first well 302a has a relatively small concaved reservoir 314 capable of receiving a protein solution and a reagent solution. And, the second well 302b has a relatively large reservoir 316 capable of receiving a reagent solution that has a higher concentration than the reagent solution deposited in the first well 302a. In particular, the first well 302a and the second well 302b share a wall 320 that physically separates the small concaved reservoir 314 from the large reservoir 316 in a manner that the small concaved reservoir 314 still has a portion of itself not counting the wall 320 or the space above the wall 320 that overlaps a portion of said second well 302b.

As a result Of the configuration and placement of the first well 302a and the second well 302b, the protein solution and the reagent solution deposited in the first well 302a can interact with the reagent solution deposited in the second well 302b via a vapor diffusion process which enables the formation Of protein crystals within the first well 302a. It should be noted that after depositing the protein solution and the reagent solutions, the openings of the wells 302 are covered by a seal such as an adhesive seal or a heat seal which can help to prevent excessive evaporation of the solutions.

The microplate 300 as shown and described herein has many structural, material and functional advantages over the aforementioned traditional microplates 100 and 200. These advantages enable the microplate 300 to be particularly well suited for protein crystallography studies. One advantage of the present invention is that the microplate 300 has the relatively small concaved reservoir 314 wherein the concave shape helps to automatically center a deposited protein solution and reagent solution within the first well 302a. Because, there are no sharp angles or corners in the first well 302a like there are in the three relatively small reservoirs 216 of the Greiner microplate 200, the deposited protein solution and reagent solution do not migrate towards the corners or edges like they do in the three relatively small reservoirs 218 (baby wells) of the Greiner microplate 200. As a result, the location of the protein solution and reagent solution near the center of the first well 302a is such that the protein crystals can be easily viewed by a researcher. In contrast, the location of the protein solution and the reagent solution near the corners or edges of the three relatively small reservoirs 216 of the Greiner microplate 200 is such that the protein crystals can not be easily viewed by a researcher.

Another advantage of the present invention is that the microplate 300 can be manufactured from a material known as cylco-olefin which has an excellent vapor barrier feature resulting in a low evaporation rate of the protein solution. In contrast, the Greiner microplate 200 is manufactured from polystyrene and as such suffers from an unacceptable rate of evaporation of the protein solution. The evaporation rate is important since many researchers monitor the crystallization of the protein solution for weeks or even months at a time. And, if the protein solution dries up at a fast rate due to evaporation then that is unacceptable to most researchers. Another drawback of the Greiner microplate 200 is that the three relatively small reservoirs 218 each of which can hold only a small amount of the protein and reagent solutions suffers from an increased evaporation rate regardless of the material of construction.

In particular, a microplate 300 manufactured from cylco-olefin would have very desirable characteristics when compared to the traditional microplates 100 and 200 that are manufactured from polystyrene and polypropylene. Table 1 illustrates some of the characteristics of cylco-olefin, polystyrene and polypropylene which are important in the field of protein crystallography.

TABLE 1

|  | Polystyrene | Polypropylene | Cylco-Olefin |
| --- | --- | --- | --- |
| Specific Gravity | 1.05 | 0.90 | 1.02 |
| Water Absorption % | 0.03–0.1 | <0.05 | 0.01 |
| Water Permeability | 3.35 | 0.2 | 0.03 |
| Softening Point ° C. | 95–100 | 95–105 | 140 |
| Strength kg/cm2 | 600 | 1600 | 900 |
| Light Transmission % | 88 |  | 92 |
| Haze % | 3 |  | 1 |
| Birefringence | High/low |  | low |

Referring to TABLE 1, it can be seen that the cylco-olefin manufactured under the Topas brand has a 100 times less water permeability characteristic and at least 10–30 times less water absorption rate when compared to polystyrene. Cylco-olefin is also highly resistant to hydrolysis, polar organics, acids & bases. More specifically, cylco-olefin has been found to be resistant to: DMSO (100% for a week), Acetone, Acetic Acid, Butanone, Ethanol, Isopropanol, Methanol, Soap solution, HCl (36%), Sulphuric acid (40%), Nitric acid (65%), Ammonia solution (33%) and Caustic soda solution (50%) (for example).

Another advantage of the present invention is that the first well 302a and the second well 302b are located on the microplate 300 in a manner that makes it possible for a standard liquid handling system to precisely locate and dispense in each well 302 the appropriate amounts of solutions. For instance, the first well 302a and the second well 302b are positioned on the microplate 300 such that a Society of Biomolecular Screening (SBS) compatible liquid handling system can automatically deposit the protein solution and reagent solutions into the wells 302a and 302b. Reference is made to the proposed SBS standards provided below for exemplary dimensions of a SBS compatible microplate 300.

Still yet another advantage of the present invention is that the microplate 300 can have a footprint that makes it possible for a standard robot handling system to handle the microplate 300. For instance, the microplate 300 can have a specific footprint that makes it possible for a SBS compatible robot handling system to handle the microplate 300. Again, reference is made to the proposed SBS standards provided below for exemplary dimensions of a SBS footprint compatible microplate 300.

The proposed SBS Standards Nos. 1–4 as downloaded from the SBS website on Feb. 6, 2000 are provided below. It should be understood that the microplate 300 of the present invention can be manufactured to have dimensions that are acceptable to a wide variety of robot handling systems and liquid handling systems which can even be one in the same.

SBS Proposed Standards:
SBS Proposed Standard 1a: Microplate Footprint
Footprint
The outside dimension of the base footprint, measured within 12.7 mm (0.5000 inches) of the outside corners, shall be as follows:
Length 127.76 mm±0.25 mm (5.0299 inches±0.0098 inches)
Width 85.48 mm±0.25 mm (3.3654 inches±0.0098 inches)
The outside dimension of the base footprint, measured at any point along the side, shall be as follows:
Length 127.76 mm±0.5 mm (5.0299 inches±0.0197 inches)
Width 85.48 mm±0.5 mm (3.3654 inches±0.0197 inches)
The footprint must be continuous and uninterrupted around the base of the plate.
Corner Radius
The four outside corners of the plate's bottom flange shall have a corner radius to the outside of 3.18 mm±1.6 mm (0.1252 inch±0.0630 inches)
SBS Proposed Standard 2a: Microplate Height-Standard Height
Plate Height
The plate height, measured from Datum A (the resting plane) to the maximum protrusion of the perimeter wells, shall be 14.35 mm±0.25 mm (0.5650 inches±0.0098 inches)
The overall plate height, measured from Datum A (the resting plane) to the maximum protrusion of the plate, shall be 14.35 mm±0.76 mm (0.5650 inches±0.0299 inches)
Top Surface
The maximum allowable projection above the top stacking surface is 0.76 mm (0.0299 inches). The top stacking surface is defined as that surface on which another plate would rest when stacked one on another.
When resting on a flat surface, the top surface of the plate must be parallel to the resting surface within 0.76 mm (0.0299 inches)
External Clearance to the Plate Bottom
The minimum clearance from Datum A (the resting plane) to the plane of the bottom external surface of the wells shall be 1 mm (0.0394 inches). This clearance is limited to the area of the wells.
SBS Proposed Standard 3a: Bottom-Outside Flange Height-Short Flange
Flange Height
The height of the bottom outside flange shall be 2.41 mm±0.38 mm (0.0948 inches±0.0150 inches). This is measured from Datum A (the bottom-resting plane) to the top of the flange.
All four sides must have the same flange height.
Flange Width
The width of the bottom outside flange measured at the top of the flange shall be a minimum of 1.27 mm (0.0500 inches).
Chamfers (Corner Notches)
The quantity and location of chamfer(s) is optional. If used, the chamfer must not include the flange.
SBS Proposed Standard 3b: Bottom-Outside Flange Height-Medium Flange
Flange Height
The height of the bottom outside flange shall be 6.1 mm±0.38 mm (0.2402 inches±0.0150 inches). This is measured from Datum A (the bottom-resting plane) to the top of the flange.
All four sides must have the same flange height.
Flange Width
The width of the bottom outside flange measured at the top of the flange shall be a minimum of 1.27 mm (0.0500 inches).
Chamfers (Corner Notches)
The quantity and location of chamfer(s) is optional. If used, the chamfer must not include the flange.
SBS Proposed Standard 3c: Bottom-Outside Flange Height-Tall Flange
Flange Height
The height of the bottom outside flange shall be 7.62 mm±0.38 mm (0.3000 inches±0.0150 inches). This is measured from Datum A (the bottom-resting plane) to the top of the flange.

All four sides must have the same flange height.
Flange Width
The width of the bottom outside flange measured at the top of the flange shall be a minimum of 1.27 mm (0.0500 inches).
Chamfers (Corner Notches)
The quantity and location of chamfer(s) is optional. If used, the chamfer must not include the flange.
SBS Proposed Standard 3d: Bottom-Outside Flange Height-Short Flange with Interruptions
Flange Height
The height of the bottom outside flange shall be 2.41 mm±0.38 mm (0.0948 inches±0.0150es). This is measured from Datum A (the bottom-resting plane) to the top of the flange.
All four sides must have the same flange height except for an allowable interruption centered along the long side.
Interruptions
Each of the long sides of the plate shall be allowed to have a single interruption or projection on center.
Each edge of the interruption shall be a minimum of 48.5 mm (1.9094 inches) from the nearest edge of the part.
The height of the flange at the interruption shall not exceed 6.85 mm (0.2697 inches)
Flange Width
The width of the bottom outside flange measured at the top of the flange shall be a minimum of 1.27 mm (0.0500 inches).
Chamfers (Corner Notches)
The quantity and location of chamfer(s) is optional. If used, the chamfer must not include the flange.
SBS Proposed Standard 3e: Bottom-Outside Flange Height-Dual Flange Heights
Flange Height
The height of the bottom outside flange shall be 2.41 mm±0.38 mm (0.0948 inches±0.0150 inches) along the short sides of the plate. This is measured from Datum A (the bottom-resting plane) to the top of the flange.
The height of the bottom outside flange shall be 7.62 mm±0.38 mm (0.3000 inches±0.0150 inches) along the long sides of the plate. This is measured from Datum A (the bottom-resting plane) to the top of the flange.
Flange Width
The width of the bottom outside flange measured at the top of the flange shall be a minimum of 1.27 mm (0.0500 inches).
Chamfers (Corner Notches)
The quantity and location of chamfer(s) is optional. If used, the chamfer must not include the flange.
SBS Proposed Standard 4a: Well Positions-96 Well Microplate
Well Layout
The wells in a 96 well microplate should be arranged as eight rows by twelve columns.
Well Column Position
The distance between the left outside edge of the plate and the center of the first column of wells shall be 14.38 mm (0.5661 inches)
The left edge of the part will be defined as the two 12.7 mm areas (as measured from the corners) as specified in SBS-1
Each following column shall be an additional 9. mm (0.3543 inches) in distance from the left outside edge of the plate.
Well Row Position
The distance between the top outside edge of the plate and the center of the first row of wells shall be 11.24 mm (0.4425 inches)
The top edge of the part will be defined as the two 12.7 mm areas (as measured from the corners) as specified in SBS-1
Each following row shall be an additional 9. mm (0.3543 inches) in distance from the top outside edge of the plate.
Positional Tolerance
The positional tolerance of the well centers will be specified using so called "True Position". The center of each well will be within a 0.71 mm (0.0280 inches) diameter of the specified location. This tolerance will apply at "RFS" (regardless of feature size).
Well Markings
The top left well of the plate shall be marked in a distinguishing manner.
The top left well of the plate can be marked with the letter A or numeral 1 located on the left-hand side of the well.
The top left well of the plate can be marked with a numeral 1 located on the upper side of the well.
Additional markings may be provided.
SBS Proposed Standard 4b: Well Positions-384 Well Microplate
Well Layout
The wells in a 384 well microplate should be arranged as sixteen rows by twenty-four columns.
Well Column Position
The distance between the left outside edge of the plate and the center of the first column of wells shall be 12.13 mm (0.4776 inches)
The left edge of the part will be defined as the two 12.7 mm areas (as measured from the corners) as specified in SBS-1
Each following column shall be an additional 4.5 mm (0.1772 inches) in distance from the left outside edge of the plate.
Well Row Position
The distance between the top outside edge of the plate and the center of the first row of wells shall be 8.99 mm (0.3539 inches)
The top edge of the part will be defined as the two 12.7 mm areas (as measured from the corners) as specified in SBS-1
Each following row shall be an additional 4.5 mm (0.1772 inches) in distance from the top outside edge of
Positional Tolerance
The positional tolerance of the well centers will be specified using so called "True Position". The center of each well will be within a 0.71 mm (0.0280 inches) diameter of the specified location. This tolerance will apply at "RFS" (regardless of feature size).
Well Markings
The top left well of the plate shall be marked in a distinguishing manner.
The top left well of the plate can be marked with the letter A or numeral 1 located on the left-hand side of the well.
The top left well of the plate can be marked with a numeral 1 located on the upper side of the well.
Additional markings may be provided.
SBS Proposed Standard 4c: Well Positions-1536 Well Microplate
Well Layout
The wells in a 1536 well microplate should be arranged as thirty-two rows by forty-eight columns.
Well Column Position
The distance between the left outside edge of the plate and the center of the first column of wells shall be 11.005 mm (0.4333 inches)
The left edge of the part will be defined as the two 12.7 mm areas (as measured from the corners) as specified in SBS-1

Each following column shall be an additional 2.25 mm (0.0886 inches) in distance from the left outside edge of the plate.

Well Row Position

The distance between the top outside edge of the plate and the center of the first row of wells shall be 7.865 mm (0.3096 inches)

The top edge of the part will be defined as the two 12.7 mm areas (as measured from the corners) as specified in SBS-1

Each following row shall be an additional 2.25 mm (0.0886 inches) in distance from the top outside edge of Positional Tolerance The positional tolerance of the well centers will be specified using so called "True Position". The center of each well will be within a 0.25 mm (0.0098 inches) diameter of the specified location. This tolerance will apply at "RFS" (regardless of feature size).

Well Markings

The top left well of the plate shall be marked in a distinguishing manner.

The top left well of the plate can be marked with the letter A or numeral 1 located on the left-hand side of the well.

The top left well of the plate can be marked with a numeral 1 located on the upper side of the well.

Additional markings may be provided.

It should be understood that the microplate 300 and specifically the first well 302a and the second well 302b of the present invention need not be circular or even dimensioned in accordance with SBS standards, instead the wells 302a and 302b may be provided in a number of alternate configurations having different cross-sectional shapes, e.g., rectangles, squares, triangles.

Figure 4A:
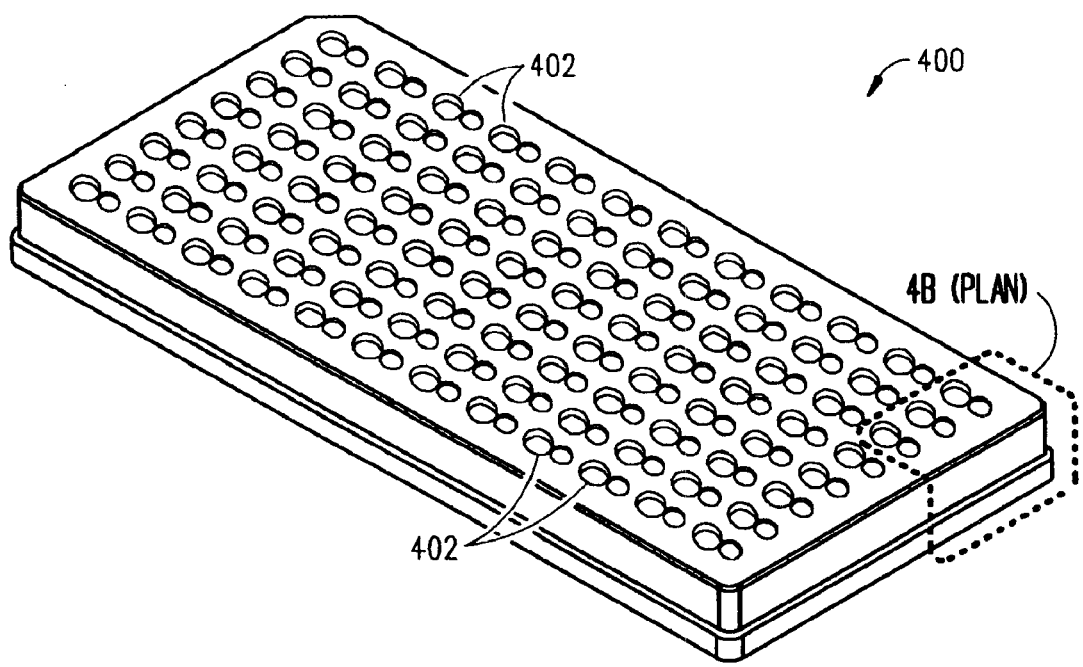
FIGS. 4A through 4C respectively illustrate a perspective view, a partial top view and a cross-sectional side view of a second embodiment of a microplate in accordance with the present invention.
Figure 4B:
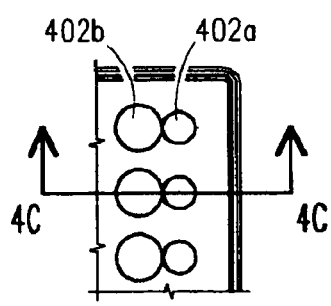
Figure 4C:
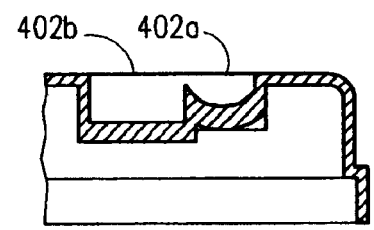

Referring to FIGS. 4A through 4C, there are respectively illustrated a perspective view, a partial top view and a cross-sectional side view of a second embodiment of a microplate 400 in accordance with the present invention. The microplate 400 is similar to microplate 300 except that the first well 402a and the second well 402b are adjacent to one another and not overlapping like the first well 302a and the second well 302b of microplate 300. The microplate 400 as shown has 96 functional wells 402.

Referring to FIGS. 5A through 5C, there are respectively illustrated a perspective view, a partial top view and a cross-sectional side view of a third embodiment of a microplate 500 in accordance with the present invention. The microplate 500 is similar to microplate 300 except that the first well 502a and the second well 502b are connected to one another by a channel 504 and not overlapping like the first well 302a and the second well 302b of microplate 300. The microplate 500 as shown has 48 functional wells 502.

Figure 6:
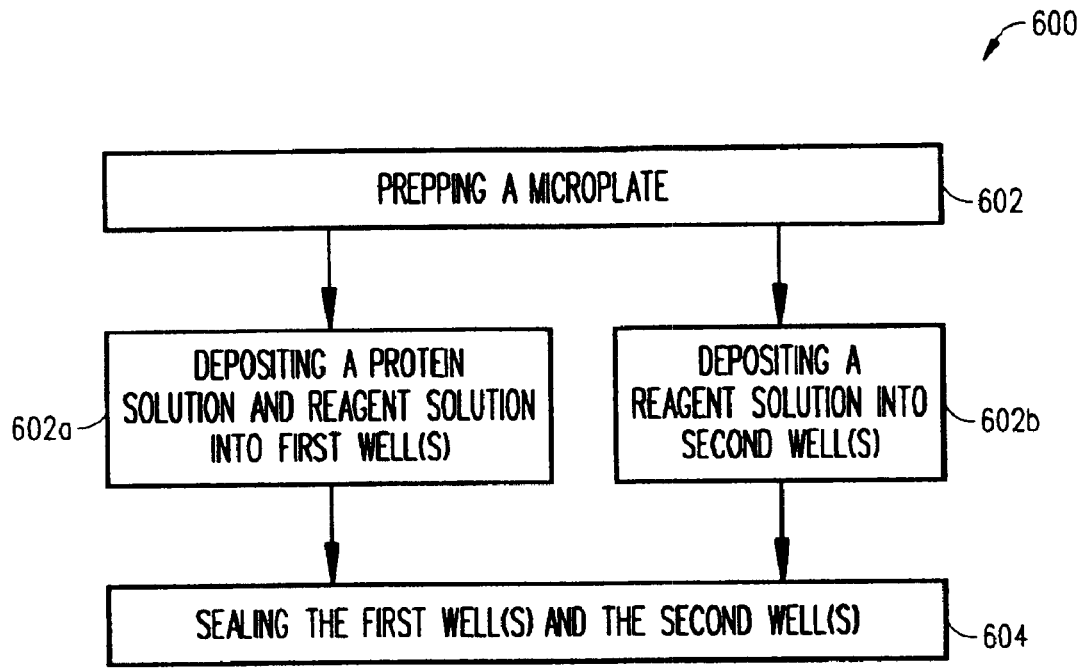
FIG. 6 is a flowchart illustrating the steps of a preferred method for using the microplate in accordance with the present invention.

Referring to FIG. 6, there is a flowchart illustrating the steps of a preferred method 600 for using the microplate 300, 400 and 500 to form protein crystals in accordance with the present invention. Although the microplates 300, 400 and 500 are described as being used to perform protein crystallography studies, it should be understood that the microplates 300, 400 and 500 can be used to perform a wide variety of studies including, for example, biochemical reaction kinetics, DNA melting point determinations, DNA spectral shifts, DNA and protein concentration measurements, excitation/emission of fluorescent probes, enzyme activities, enzyme-cofactor assays, homogeneous assays, drug metabolite assays, drug concentration assays, dispensing confirmation, volume confirmation, solvent concentration confirmation and salvation confirmation. Accordingly, the microplates 300, 400 and 500 and preferred method 600 should not be construed in such a limited manner.

Beginning at step 602, the microplate 300, 400 and 500 is prepped (step 602) by depositing (step 602a) a protein solution and a reagent solution into the first well 302a, 402a and 502a and depositing (step 602b) a reagent solution into the second well 302b, 402b and 502b. Again, a liquid handling system can be used to deposit the protein solution and the reagent solution into the first well 302a, 402a and 502a and to deposit the reagent solution into the second well 302b, 402b and 502b. In particular, a SBS compatible liquid handling system can be used to deposit the various solutions into the wells 302, 402 and 502 provided the wells are located in accordance with a SBS well location standard (for example).

At step 604, the microplates 300, 400 and 500 and, in particular, the wells 302, 402 and 502 are sealed or covered with a top, a heat seal or an adhesive tape (for example) to help prevent evaporation. The heat seal is particularly well suited for screening applications and the adhesive seal is particularly well suited for optimization and growth of protein crystals.

At this point, the prepped and sealed microplate 300, 400 and 500 is assembled in a manner to enable the protein solution and the reagent solution within the first well 302a, 402a and 502a to interact with the higher concentration of reagent solution within the second well 302b, 402b and 502b via a vapor diffusion process which leads to the formation of protein crystals within the first well 302a, 402a and 502a. For example, the first wells 302a, 402a and 502a can hold around 2–20 μl of a protein solution and a lower concentrated reagent solution and the second well 302b, 402b and 502b can hold up to 0.5 ml of a higher concentrated reagent solution. The uneven concentration between the reagent solution in the first well 302a, 402a and 502a and the reagent solution in the second well 302b, 402b and 502b drives a natural vapor diffusion process towards equilibrium. During the crystallization process, the protein solution and reagent solution in first well 302a, 402a and 502a loses water content through vapor diffusion and as such decreases in volume. As the volume decreases, the chemical contents including the protein in the first well 302a, 402a and 502a get increasingly concentrated. During this progression of increasing concentration, and given the right variables (e.g., chemicals present, temperature) a protein crystal may form.

Figure 7:
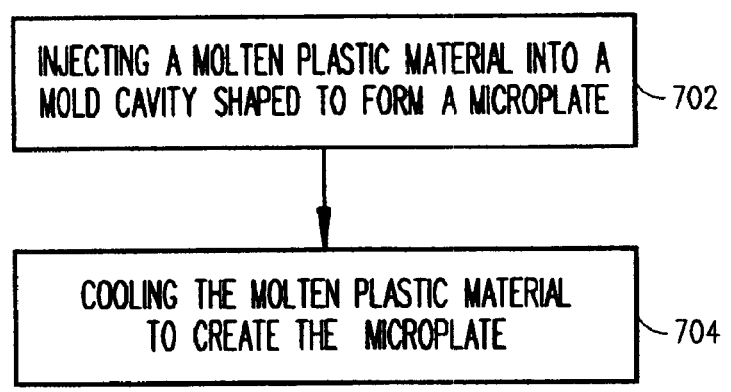
FIG. 7 is a flowchart illustrating the steps of a preferred method for making the microplate in accordance with the present invention.

Referring to FIG. 7, there is a flowchart illustrating the steps of a preferred method 700 for making the microplate 300, 400 and 500 in accordance with the present invention. Beginning at step 702, a molten plastic material is injected into a mold cavity that includes sections shaped to form the microplate 300, 400 and 500. Preferably, the plastic material is made from cylco-olefin, polystyrene or polypropylene and the mold cavity is shaped to form a SBS compatible microplate 300, 400 and 500.

At step 704, the molten plastic material is cooled to create the microplate 300, 400 and 500. Again, the microplate 300, 400 and 500 can be sized to enable it to be handled by a robotic handling system and a liquid handling system. In particular, the robotic handling system can be a SBS compatible robotic handling system and the liquid handling system can be a SBS compatible handling system.

Although several embodiments of the present invention has been illustrated in the accompanying Drawings and described in the foregoing Detailed Description, it should be understood that the invention is not limited to the embodiments disclosed, but is capable of numerous rearrangements, modifications and substitutions without departing from the spirit of the invention as set forth and defined by the following claims.

What is claimed is:

1. A microplate, comprising:
a frame including a plurality of wells formed therein, each well including:
- a first well having a relatively small reservoir with a substantially concaved bottom; and
- a second well having a relatively large reservoir, wherein said first well is not entirely located within said second well nor is said first well entirely located outside of said second well but instead said first well and said second well share a wall that physically separates the small reservoir from the large reservoir in a manner that the small reservoir still has a portion of itself not counting the wall or space above the wall that overlaps a portion of said second well.

2. The microplate of claim 1, wherein said frame has a footprint sized to be handled by a robotic handling system.

3. The microplate of claim 1, wherein each well is positioned on said frame such that a liquid handling system can automatically deposit a sample solution into the small reservoir of said first well and can automatically deposit a reagent solution into a large reservoir of said second well.

4. The microplate of claim 1, further comprising a seal that is positioned over said plurality of wells.

5. The microplate of claim 1, wherein said microplate is manufactured from cyclo-olefin.

6. The microplate of claim 1, wherein said frame and said plurality of wells form a multi well high-throughput protein crystallography plate.

7. A protein crystallography plate, comprising:
a frame made from cyclo-olefin that includes a plurality of wells formed therein, each well is also made from cyclo-olefin and includes:
- a first well including a relatively small reservoir having a substantially concaved bottom for receiving a protein solution and a reagent solution; and
- a second well including a relatively large reservoir for receiving a reagent solution that has a higher concentration than the reagent solution within said first well, wherein the protein solution and the reagent solution within said first well interact with the reagent solution within said second well via a vapor diffusion process which enables the formation of protein crystals within said first well, wherein said first well is not entirely located within said second well nor is said first well entirely located outside of said second well but instead said first well and said second well share a wall that physically separates the small reservoir from the large reservoir in a manner that the small reservoir still has a portion of itself not counting the wall or space above the wall that overlaps a portion of said second well.

8. The protein crystallography plate of claim 7, wherein said frame has a footprint sized to be handled by a robotic handling system.

9. The protein crystallography plate of claim 7, wherein each well is positioned on said frame such that a liquid handling system can automatically deposit the protein solution and the reagent solution into the small reservoir or said first well and can automatically deposit the reagent solution into the large reservoir or said second well.

* * * * *